US 6,661,506 B2

(12) United States Patent
Chang

(10) Patent No.: US 6,661,506 B2
(45) Date of Patent: Dec. 9, 2003

(54) ENGINE BEARING INSPECTION SYSTEM

(75) Inventor: Tzyy-Shuh Chang, Ann Arbor, MI (US)

(73) Assignee: OG Technologies, Inc., Ann Arbor, MI (US)

( * ) Notice: Subject to any disclaimer, the term of this patent is extended or adjusted under 35 U.S.C. 154(b) by 146 days.

(21) Appl. No.: 09/934,151

(22) Filed: Aug. 21, 2001

(65) Prior Publication Data

US 2002/0024658 A1 Feb. 28, 2002

Related U.S. Application Data

(60) Provisional application No. 60/227,538, filed on Aug. 24, 2000.

(51) Int. Cl.[7] .............................................. G01N 21/00
(52) U.S. Cl. .................................................. 356/237.2
(58) Field of Search ........................... 356/237.1, 237.2, 356/237.3, 237.4, 237.5, 241.1, 626, 601; 382/141, 143

(56) References Cited

U.S. PATENT DOCUMENTS

| | | | | |
|---|---|---|---|---|
| 3,761,186 A | * | 9/1973 | Wason ...................... 356/241.1 |
| 4,440,496 A | | 4/1984 | Milana ........................ 356/241 |
| 4,557,598 A | | 12/1985 | Ono et al. ................... 356/241 |
| 4,561,731 A | | 12/1985 | Kley ........................... 350/510 |
| 4,622,462 A | | 11/1986 | Eaton et al. ................. 250/236 |
| 4,725,883 A | | 2/1988 | Clark, Jr. et al. ........... 358/100 |
| 4,750,045 A | * | 6/1988 | Ohara et al. ................. 358/494 |
| 4,816,923 A | * | 3/1989 | Saotome ..................... 358/489 |
| 4,849,643 A | | 7/1989 | Mundy ........................ 250/560 |
| 4,861,984 A | * | 8/1989 | West ........................ 356/241.1 |
| 4,967,092 A | | 10/1990 | Fraignier et al. ........... 250/560 |
| 5,008,555 A | | 4/1991 | Mundy ........................ 250/560 |
| 5,017,798 A | | 5/1991 | Murakami et al. .......... 250/572 |
| 5,060,063 A | | 10/1991 | Freeman ..................... 358/101 |
| 5,078,955 A | | 1/1992 | Hydeman et al. ........... 376/248 |
| 5,237,444 A | * | 8/1993 | Schermer ..................... 359/202 |
| 5,245,411 A | | 9/1993 | Dury ........................... 356/446 |
| 5,317,387 A | | 5/1994 | Van Hengel et al. ....... 356/372 |
| 5,392,113 A | | 2/1995 | Sayka et al. ................. 356/237 |
| 5,416,589 A | | 5/1995 | Lysogorski .................. 356/371 |
| 5,438,417 A | | 8/1995 | Busch et al. ................. 356/394 |
| 5,448,350 A | | 9/1995 | Kohno ........................ 356/237 |
| 5,465,153 A | | 11/1995 | Ladewski .................... 356/376 |
| 5,519,494 A | | 5/1996 | Akamatsu et al. .......... 356/371 |
| 5,521,692 A | | 5/1996 | Bares .......................... 355/311 |
| 5,652,617 A | | 7/1997 | Barbour ....................... 348/85 |
| 5,699,152 A | | 12/1997 | Fedor et al. ................. 356/237 |
| 5,717,455 A | | 2/1998 | Kamewada ................... 348/85 |
| 5,774,212 A | | 6/1998 | Corby, Jr. ................... 356/237 |
| 5,777,731 A | | 7/1998 | McBride ..................... 356/243 |
| 6,002,495 A | * | 12/1999 | Rombult et al. ............ 358/488 |
| 6,002,524 A | * | 12/1999 | Schubert ..................... 359/642 |
| 6,057,537 A | * | 5/2000 | Schubert et al. ............ 250/205 |
| 6,075,591 A | * | 6/2000 | Vokhmin ................. 356/239.1 |
| 6,094,287 A | * | 7/2000 | Li ............................... 359/211 |
| 6,108,025 A | * | 8/2000 | Li et al. ...................... 347/256 |
| 6,392,754 B1 | * | 5/2002 | Pingel et al. ............ 356/239.1 |
| 6,462,815 B1 | * | 10/2002 | Drabarek et al. ........ 356/241.1 |

* cited by examiner

Primary Examiner—Michael P. Stafira
Assistant Examiner—Juan D Valentin, II
(74) Attorney, Agent, or Firm—Dykema Gossett PLLC

(57) ABSTRACT

An inspection system is used to view an image of the inside diameter (ID) of an engine bearing. The inspection system includes a stationary line scan camera, a pivoting mirror, a scanning mirror and a stationary mount. The engine bearing is placed in the stationary mount such that the bearing remains motionless throughout the entire scanning process. The light line generator produces a light line that initially contacts a beam splitter. The beam splitter then guides the light line onto the pivoting mirror, which then directs the light line onto one of a pair of stationary mirrors and then finally onto the scanning mirror. The scanning mirror will sweep the light line across a portion of the engine bearing ID surface. The light line will generate reflected images of the ID surface. These reflected images will return along the light line's path; however, instead of being directed back into the light line generator by the beam splitter, the reflected images will pass through the beam splitter. Once the reflected images pass through the beam splitter, they will journey through the lens and into the stationary line scan camera. From the stationary line camera, the reflected images can be viewed on a monitor and recorded for future use.

28 Claims, 5 Drawing Sheets

| | 0.25 sec. | 0.2 sec. | 0.1 sec. | 0.2 sec. |
|---|---|---|---|---|
| Scanning Mirror | Move to initial position | Scan half (move at 40 rpm) | Move to 2nd start point (move at 200 rpm) | Scan half (move at 40 rpm) |
| Scanning Mirror RPM Profile | | | | |
| Pivoting Mirror | Move to initial position | | Move to 2nd position | |
| Pivoting Mirror RPM Profile | | | | |

ENGINE BEARING INSPECTION SYSTEM

RELATED APPLICATIONS

This application claims the benefit of U.S. provisional application Ser. No. 60/227,538 filed Aug. 24, 2000, herein incorporated by reference in its entirety.

BACKGROUND OF THE INVENTION

1. Technical Field

The present invention relates generally to an inspection system, and more particularly, to an engine bearing inspection system and to a method to inspect engine bearings.

2. Description of the Related Art

In motor vehicles, engine bearings serve to withstand the immense mechanical loads generated by crankshaft movement and to protect the crankshaft journals from physically contacting the engine block. Because of the tremendous loads on the inner diameter (ID) surface of these engine bearings, the ID surfaces must remain free from impurities and defects, such as dust, scratches and chips at all times, including during their own manufacturing process. Currently, bearing manufacturers inspect the ID surfaces for defects and impurities with human inspectors. Because of high production demands, manufacturers typically produce eighty bearings every minute. Because of this high throughput, it is not possible for the human inspectors to inspect every bearing for impurities or defects. To increase the numbers of bearings inspected, bearing manufacturers have attempted to inspect the ID surfaces with imaging technology. Conventional inspection approaches have shortcomings.

One approach taken to inspect an inside diameter surface in the context of a can includes using at least three cameras to view the entire ID surface as seen by reference to U.S. Pat. No. 5,699,152 issued to Fedor et al. The expense incurred in using at least three cameras exemplifies an obvious flaw with the approach taken in Fedor et al. Another flaw caused by using multiple cameras (such as in Fedor et al.), in general, involves the generation of internal reflections. Internal reflections are caused by the use of multiple light sources in the imaging process that generate internal reflections, for example within the concave-shaped bearing. The internal reflections, in turn, generate undesirable dark strips on the resulting images of the ID surface. The dark strips will prevent the imaging system from detecting impurities or defects located on these obscured portions of the ID surface images.

Another imaging technology method used to inspect ID surfaces utilizes a single camera. Yet in order to view the bearing in its entirety, either the camera or the bearing under inspection must move to perform a complete scan of the entire surface ID. Moving the bearing slows throughput because extra time must be allotted for the bearing's motion and the extra movement exposes the bearing to an increased risk of damage. Likewise, moving the camera to scan the bearing also slows throughput because extra time must be allotted for the camera's motion. Furthermore, in order for the camera to move, the system requires long cables to power and operate the camera. These long cables generate electromagnetic interference that reduces the image quality of the inspection system. Also, the repetitive movement of the camera causes premature wear or breakage of the camera cables. This wear or breakage usually results in the costly replacement of the camera cables.

These disadvantages have made it apparent that a new technique to inspect engine bearings for impurities or defects is needed.

SUMMARY OF THE INVENTION

One object of the present invention is to provide a solution to one or more of the above mentioned problems. One advantage of the present invention is that only one camera is needed to acquire the image beam of the inside diameter (ID) surface of a component under inspection such as an engine bearing. Another advantage of the present invention is that the camera remains stationary, thereby eliminating the possibility of excessive wear, breakage and tangling of the camera cables. Another advantage of the present invention is the elimination of internal reflection interference in the resulting image, compared to conventional multi-camera, multi-light source arrangements. Another advantage of the present invention is that the component under inspection remains stationary throughout the scanning process, thus reducing the possibility of damaging the component by excessive movement. Still another advantage of the present invention is that an increased percentage of engine bearings can be inspected for impurities and defects without decreasing throughput.

In one aspect of the invention, an inspection system is provided that is used to view an image of an inside diameter (ID) surface of a component, such as an engine bearing. The system includes a mount, optics, and a line scan camera. The mount is configured to hold the component in a first fixed position during a scanning interval. The optics are configured to direct a source light beam, such as a light line, to the ID surface wherein an image beam is produced. The line scan camera is disposed in a second fixed position, and is configured to acquire the image beam so produced. The component under inspection and the line scan camera are both stationary during the scanning interval, thereby reducing or eliminating one or more of the problems as set forth in the Background.

In a preferred embodiment, the optics comprise a first mirror, and a scanning mirror. The first mirror is moveable between a first position and a second position, while the scanning mirror is moveable from a first start orientation to a first stop orientation. The first mirror, which may be a pivoting mirror, when in the first position, is configured to direct the source light beam to the scanning mirror by way of a first stationary mirror. The scanning mirror is configured to scan a portion of the ID surface using the source light beam when moving from the first start orientation to the first stop orientation.

In a still further preferred embodiment, the scanning mirror further includes a respective second start and stop orientation. The first mirror, when in the second position, is configured to direct the source light beam to the scanning mirror by way of a second stationary mirror. The scanning mirror is configured to scan the remainder of the ID surface of the component under inspection when moving from the second start orientation to the second stop orientation. In a constructed embodiment, the area of the ID surface scanned by the scanning mirror by way of the first stationary mirror is about one-half the total area, while that scanned by the scanning mirror by way of the second stationary mirror comprises the other half.

A method for inspecting a component is also presented.

BRIEF DESCRIPTION OF THE DRAWINGS

The present invention will now be described by way of example, with reference to the accompanying drawings, in which.

DETAILED DESCRIPTION OF A PREFERRED EMBODIMENT

Figure 1:
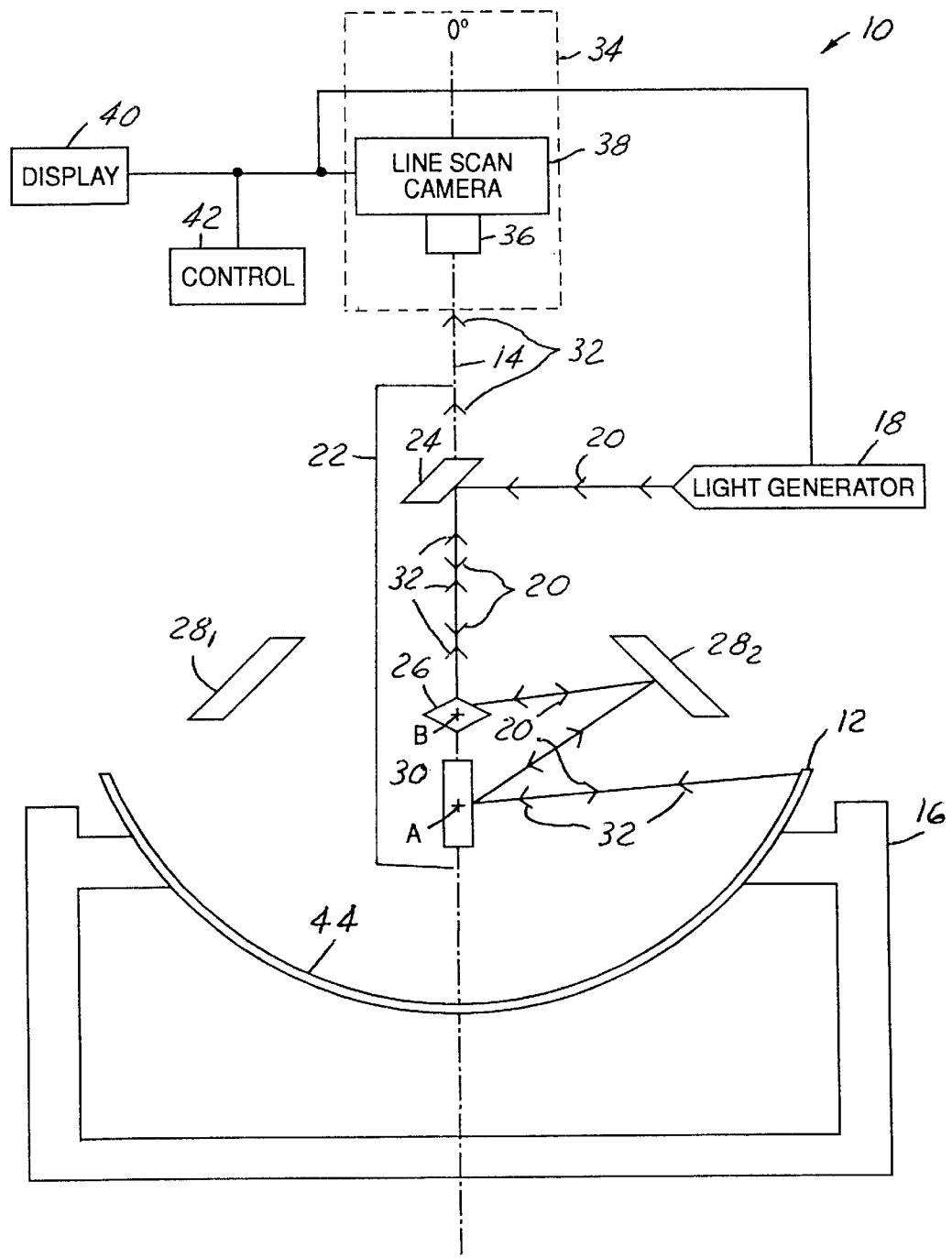
FIG. 1 is a side view of a first embodiment of an inspection system in accordance with the present invention, shown in a first position for scanning a first half of the bearing.

In the following figures, the same reference numerals identify identical components in the various views. FIG. 1 illustrates an inspection system 10 according to the present invention. System 10, in one embodiment, is particularly suited for inspection of components used in an automotive environment. However, the present invention may also be applied to various other uses that may require an inspection system, including inspection of other parts having an inside diameter (ID) surface.

Referring to FIG. 1, a side view of an inspection system 10 in accordance with one embodiment of the present invention is illustrated. System 10 is configured for inspecting a component having an inside diameter (ID surface). In the illustrated embodiment, such component comprises an engine bearing, particularly one-half of a split type main bearing. One skilled in the art will realize that system 10 may include one representation of many possible systems to inspect an engine bearing. The component to be inspected, such as engine bearing 12 (best shown in FIG. 2), may be placed symmetrically with respect to a viewing axis 14 on a stationary mounting platform 16. One skilled in the art, however, will realize that engine bearings are merely one type of many possible components that can be inspected using system 10. In addition, one skilled in the art will realize that engine bearing 12 can be positioned asymmetrically relative to axis 14, depending upon which portion of engine bearing 12 requires inspection.

FIG. 1 also depicts a light line generator 18 configured to produce a light line 20, and an optics system 22. Optics system 22 includes a beam splitter 24, a pivoting mirror 26, a pair of stationary mirrors $28_1$, $28_2$ that are symmetrically positioned about viewing axis 14, and a scanning mirror 30. FIG. 1 further illustrates an image beam 32, an image acquisition means 34 comprising a lens 36 and a stationary line scan camera 38, a display monitor 40 and a control module 42 that houses the logic to drive generator 18 and control various components of optics system 22.

Figures 2, 4:
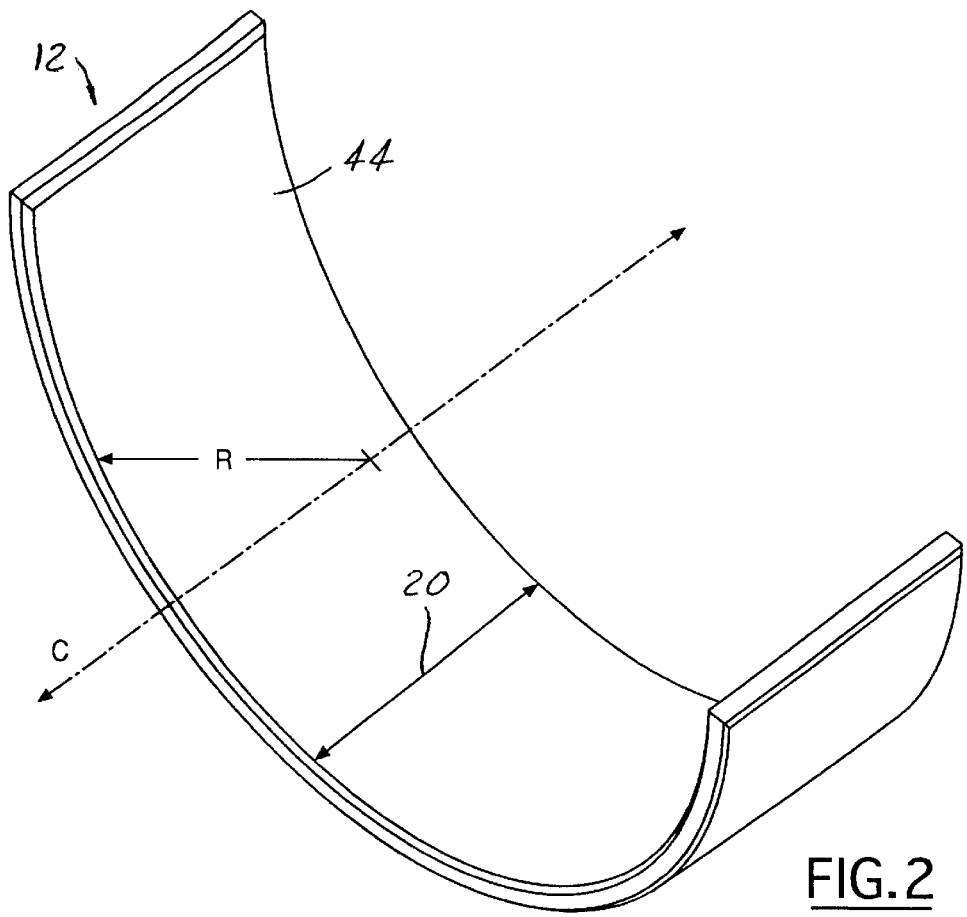
FIG. 2 is a perspective view of an engine bearing, showing an inside diameter (ID) surface.
FIG. 4 is a timing diagram illustrating the movement and respective speed profiles of the pivoting and scanning mirrors.

Referring to FIG. 2, a perspective view of engine bearing 12 is shown. Axis C is the cylindrical axis of engine bearing 12. An engine bearing ID surface 44 is the surface of engine bearing 12 that is scanned by system 10 for imperfections such as, but not limited to, scratches, nicks, chips, lint or dirt. Light line 20 is also shown in diagrammatic fashion.

Referring again to FIG. 1, generator 18 is configured to produce light line 20 for illuminating the ID surface 44 of bearing 12. In the illustrated embodiment, generator 18 is controlled by control module 42 to activate and create light line 20. One skilled in the art will realize that generator 18 may include one of a plurality of light sources that can be used in conjunction with system 10. Types of light sources include, but are not limited to, laser, optical fiber or focused light. The type of light used depends upon, among other factors, the type and shape of the component being inspected. Generator 18 is positioned in a manner such that light line 20 is directed to beam splitter 24.

Optics system 22 is configured generally to direct a source light beam from generator 18 to the ID surface 44 wherein the image beam 32 is produced. Optics 22 includes a beam splitter 24 that is centered on axis 14 wherein axis 14 coincides with the center of engine bearing 12. Once light line 20 reaches beam splitter 24, light line 20 will be directed to pivoting mirror 26.

Pivoting mirror 26 is centered on axis 14. Pivoting mirror 26 is moveable between a first position and a second position. In the illustrated embodiment, controller 42 is configured to move pivoting mirror 26 to the first position to scan a first half (i.e., the right hand side) of the bearing, and, to further move mirror 26 to its second position to scan the other half of ID surface 44 (i.e., the left hand side). It should be appreciated that pivoting mirror 26 may comprise one of a plurality of highly reflective surfaces known to those of ordinary skill.

Stationary mirror $28_1$ and mirror $28_2$ can be any one of a plurality of highly reflective surfaces known to those of ordinary skill.

Scanning mirror 30 can be substituted with any one of a plurality of highly reflective surfaces, as one skilled in the art will realize. Scanning mirror 30, in a preferred embodiment, is positioned such that its rotating axis A is parallel to the rotating axis of pivoting mirror 26, namely rotating axis B. Scanning mirror 30 is moveable so as to sweep from a first start orientation to a first stop orientation, and to further sweep from a second start orientation to a second stop orientation. Scanning mirror 30 has an axis of rotation, designated "A," that is preferably coincident with the cylindrical axis "C" of the component (e.g., bearing 12). This will be described in greater detail below.

In general operation, the pivoting mirror 26, when in the first position, is configured to direct the source light beam (i.e., light line 20) to the scanning mirror 30 by way of first stationary mirror $28_1$. Scanning mirror 30 is configured to scan the ID surface 44 using the source light beam, namely light line 20, when the scanning mirror is moved via controller 42 from the above-mentioned first start orientation through to the above-mentioned first stop orientation. In one embodiment, this action scans one-half of the bearing. Pivoting mirror 26, in its second position, is configured to direct the source light beam, namely light line 20, to scanning mirror 30 via second stationary mirror $28_2$. The scanning mirror 30 is configured to scan the ID surface 44 when it is moved under control of controller 42 from its second start orientation through to its second stop orientation using the source light beam.

EXAMPLE

In the embodiment of FIG. 1, for purposes of facilitating description, the twelve o'clock position may be taken as the 0-degree reference, with increasing degree values to be taken in the clockwise (CW) direction. Pivoting mirror 26 initially faces about 45-degrees; however, this direction can be altered as needed. Again using the 12 o'clock position as the 0-degree reference, scanning mirror 30 is initially positioned in a first start orientation, which is at 81 degrees in the present embodiment. That is, the mirror is positioned so that a light line 20 is redirected to about an 81 degree position, relative to a 12 o'clock position being 0 degrees.

The first start orientation thus provides a starting point for scanning mirror 30 to scan the right side of ID surface 44.

After controller causes mirror 26 and mirror 30 to assume the positions/orientations described above, it causes generator to be activated and produce light line 20. After light line 20 reaches pivoting mirror 26, it will be directed to stationary mirror $28_1$. From stationary mirror $28_1$, light line 20 will travel to scanning mirror 30. Light line 20, when it leaves scanning mirror 30, will travel to and contact the engine bearing inside diameter (ID) surface 44 at approximately 90-degrees.

While scanning mirror 30 is controlled to rotate clockwise, it will redirect light line 20 in a clockwise scanning motion. When light line 20 scans ID surface 44, an image beam 32 of ID surface 44 is generated. Image beam 32 initially will retrace light line's 20 path. Image beam 32 travels from the ID surface 44 and strikes scanning mirror 30. Scanning mirror 30 guides image beam 32 to stationary mirror $28_1$, which in turn directs image beam 32 to pivoting mirror 26. Unlike light line 20, however, beam splitter 24 will not divert image beam 32. Instead, image beam 32 will pass through beam splitter 24 and into lens 36. Lens 36 can magnify and focus image beam 32 if needed. Once past lens 36, image beam 32 will travel to stationary camera 38, where it may be acquired, and, thereafter processed by either (i) image processing software in control module 42 or (ii) by an operator using display monitor 40 and be recorded for later analysis. Both lens 36 and stationary camera 38 may be centered on axis 14. Further, one skilled in the art will realize that recording can be accomplished by many methods including, but not limited to, electronically or magnetically. Scanning mirror 30 will continue rotating clockwise under control of control module 42 until reaching the first stop orientation. In the first stop orientation, light line 20 is directed by mirror 30 to the 180-degree reference. The scanning mirror 30 itself is rotated about 47 degrees.

Figure 3:
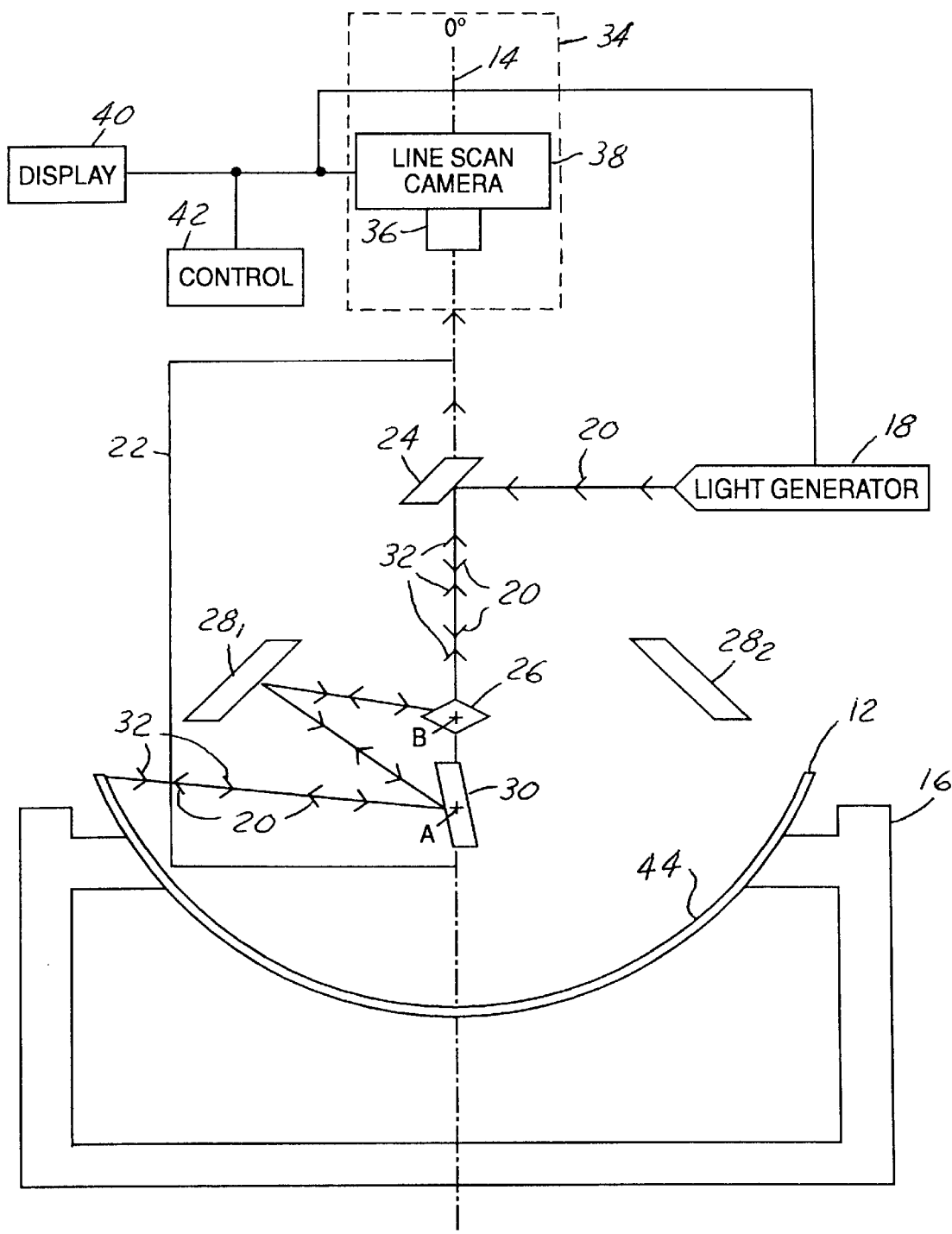
FIG. 3 is a side view of the inspection system of FIG. 1 in a second position for scanning the other half of the bearing.

Referring to FIG. 3, once the right side of engine bearing 12 is scanned completely, system 10 is ready to commence scanning the left side of the engine bearing 12. Controller 42 controls the initialization of optics system 22 (e.g., to initial or start orientations) the light generator 18, and image acquisitions means 34. To effect scanning of the left side as viewed in FIGS. 1 and 3, controller 42 causes pivoting mirror 26 to rotate from its first position (i.e., the 45-degree position) to its second position (i.e., 315-degree position). One skilled in the art will realize that the first position and the second position of pivoting mirror 26 do not have to be at 45- and 315-degrees, respectively, so long as the two positions used are symmetric with respect to the 0-degree axis. Controller 42 will further cause scanning mirror 30 to rotate from its prior position where it directed light line 20 to the 180-degree position (i.e., where it finished its first scan) to a position where it will direct light line 20 to an approximately 284-degree position. This will mark the second start orientation for scanning the remainder of bearing 12. Once 30 pivoting mirror 26 and scanning mirror 30 are initialized for scanning the left side, as described above, the scanning process begins again, this time with scanning mirror 30 being controlled to travel in a clockwise (CW) direction, again for about 47 degrees, until it reaches its second stop orientation (i.e., where the light line 20 is directed to an approximately 180-degree position). Once the scan of the left side of engine bearing 12 is complete, both scanning mirror 30 and pivoting mirror 26 return to their original positions, as described above.

Referring to FIG. 4, a timing diagram illustrating the time required for scanning mirror 30 and pivoting mirror 26 to complete a full scanning cycle is shown. Also shown is the rpm profile of scanning mirror 30 and pivoting mirror 26 through their various positions. Control module 42 houses the logic necessary to command the operation of motors used in moving mirrors 26 and 30. It takes system 10 approximately 0.25 seconds to move scanning mirror 30 and pivoting mirror 26 into their initial start positions at 81-degrees and 45-degrees respectively; however, one skilled in the art will realize that the amount of time system 10 takes to initialize scanning mirror 30 and pivoting mirror 26 depends upon other system components, such as the type of motor used. During this time, the rpm profiles of scanning mirror 30 and pivoting mirror 26 reach their first peak at approximately 200 rpm. One skilled in the art will realize that other rpm values can be used in conjunction with system 10 as dictated by the components used. Once the scan of the right side of engine bearing 12 begins, the rpm output of pivoting mirror 26 is zero because pivoting mirror 26 is stationary during scanning. The speed of scanning mirror 30 drops down to 40 rpm to complete the scanning motion. The scan of the right side of engine bearing 12 takes approximately 0.2 seconds, yet one skilled in the art will realize that this value depends upon the components used and also can be altered as needed. However, the foregoing being said, the improvement occasioned by the present invention results from keeping both the camera and the component stationary. This allows the improved scanning speed referred to above. Once the scan of the right side of engine bearing 12 is complete, scanning mirror 30 and pivoting mirror 26 are initialized once again in preparation for the scan of the left side of engine bearing 12. In 0.1 second, the motors will place scanning mirror 30 in the 284-degree position and pivoting mirror 26 in the 315-degree position the respective start orientations for the left hand side scan. During this initialization, the rpm values once again achieve their maximum value at approximately 200 rpm. From this initial position, the rpm value for pivoting mirror 26 again drops to zero because pivoting mirror 26 does not move during the scanning process. Similarly, the rpm value for scanning mirror 30 drops to 40 rpm during the scan of the left side of engine bearing 12. In 0.2 seconds, the scan of the left side of engine bearing 12 is complete.

Figure 5:
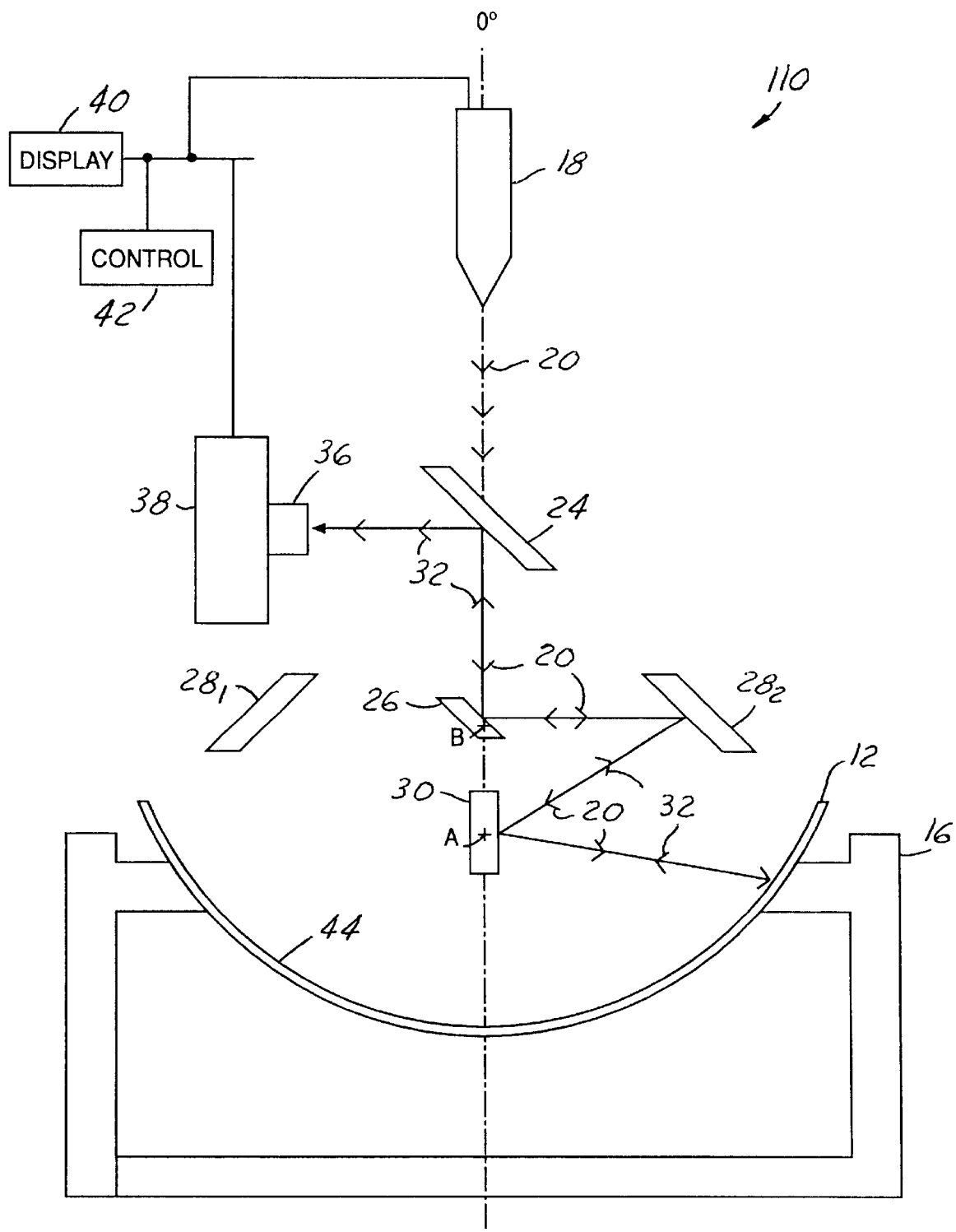
FIG. 5 is a side view of an alternate embodiment of an inspection system in accordance with the present invention wherein a light source is centered about the bearing under inspection.

Referring to FIG. 5, an alternative embodiment of an engine bearing inspection system designated 110 is presented. Instead of being stationed directly above engine bearing 12, stationary camera 38 and lens 36 are positioned off to the side while generator 18 assumes the position above engine bearing 12. In this embodiment, light line 20 will flow through beam splitter 24 onto pivoting mirror 26. From pivoting mirror 26, light line 20 will be directed as described in reference to FIGS. 1–3 above. Image beam 32 also will follow the same general trajectory as described in reference to FIGS. 1 and 2 above, except that beam splitter 24 will direct image beam 32 into lens 36, where it then travels to stationary camera 38.

Figure 6:
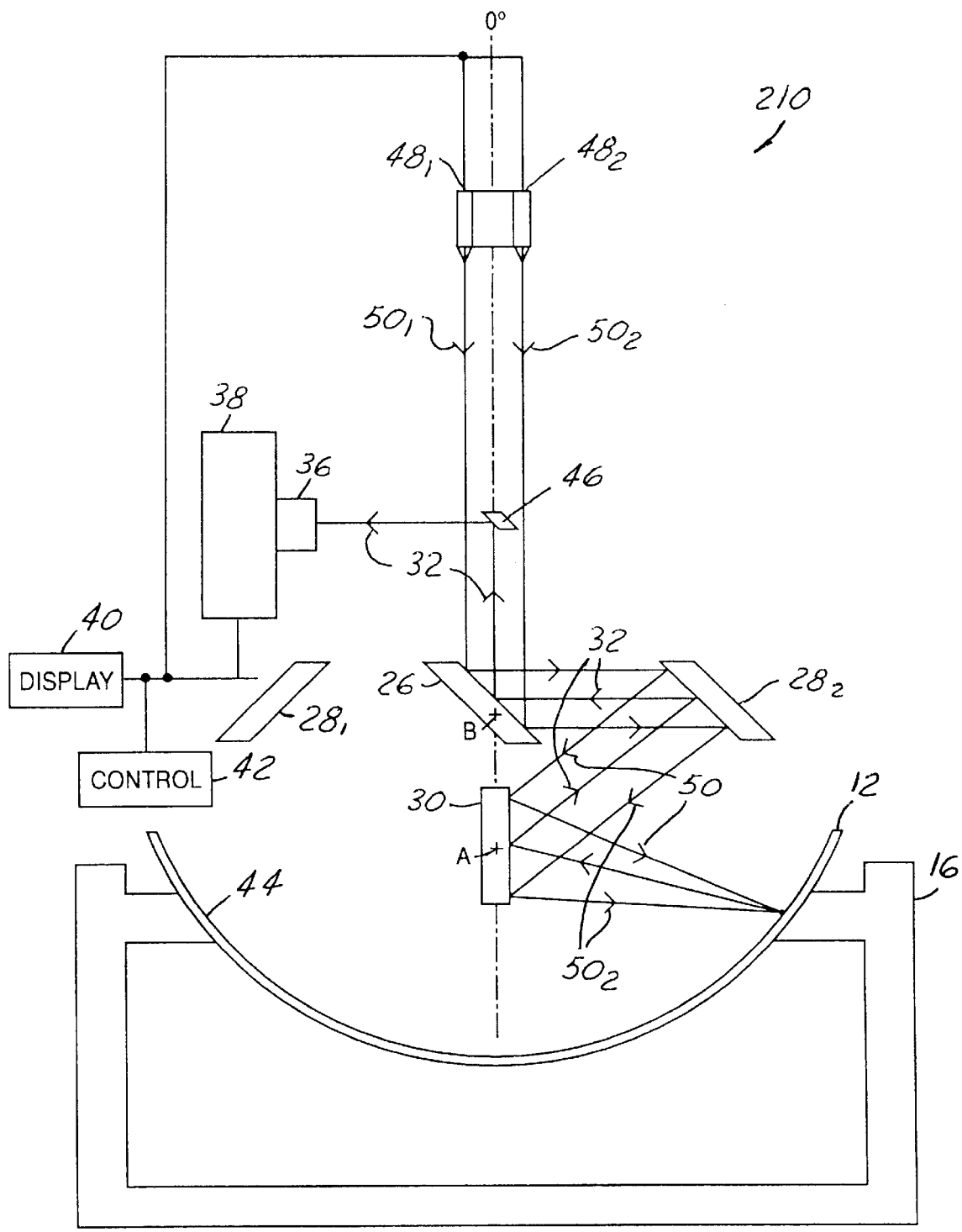
FIG. 6 is yet another embodiment of an inspection system according to the present invention.

Referring to FIG. 6, yet another alternative embodiment of an engine bearing inspection system, herein designated 210, is illustrated. A first mirror 46, as described in reference to FIGS. 1–3 above, replaces beam splitter 24. In addition, two light line generators $48_1$, $48_2$ are symmetrically mounted above first mirror 46 such that the generated light lines $50_1$, $50_2$ do not contact the first mirror 46. One skilled in the art will realize that a single light line generator can be used as long as the generated light line is symmetrically wider on both sides than first mirror 46. Light lines $50_1$, $50_2$ will flow through first mirror 46 and contact pivoting mirror 26. From pivoting mirror 26, light lines 50₁, 50₂ will proceed as described in reference to FIGS. 1 and 2 above. Image beam 32 will also be directed as described in reference to FIGS. 1 and 2 above except that instead of bypassing beam splitter 24, image beam 32 will be guided by first mirror 46 into the lens 36.

Those skilled in the art will appreciate that the source light path and the image path can be rearranged so that the specific example values provided above may vary. For instance, in an alternative embodiment, the source lighting and imaging paths may be slightly different so that the pivoting mirror 26 faces a 42.12 degree direction and a 317.88 degree direction, instead of a 45 degree direction and 315 degree direction, respectively, in preparation for right hand side and left hand side scans of bearing 12. In addition, it should be understood that scanning mirror 30 is located at, and rotates with respect to a cylindrical axis, or best fitted cylindrical axis, of a full, semi, partial, or near cylindrical part surface being inspected. That is, the cylindrical axis C of the bearing 12 (or best fit axis of any particular part) is substantially coincident with the axis of rotation A of the scanning mirror 30. In addition, it will be further appreciated that in the embodiments described herein, that the path taken by the source light beam and the path taken by the image beam are substantially identical from the ID surface 44 all the way to beam splitter 24. Moreover, those of ordinary skill in the art will appreciate that there exists no perfect cylindrical surfaces and reasonable tolerances should be given to the meanings of "identical" and "perpendicular," as described herein.

Further, those skilled in the art shall vision the applications of the invented system in parts with cylindrical ID surfaces other than engine bearings, such as, but not limited to, the cylinder bores in internal combustion engines.

The invented system, wherever necessary, can be reduced to scan a portion of an engine bearing, or a part of the like, with only one of the stationary mirrors, the scanning mirror. In this case, the light will be directed directly from the beam splitter to the stationary mirror, without passing through the pivoting mirror.

From the foregoing, it can be seen that a new and improved inspection system for engine bearings has been brought to the art. It is to be understood that the preceding description of the preferred embodiments is merely illustrative of some of the many specific embodiments that represent applications of the principles of the present invention. Other arrangements would be evident to those skilled in the art without departing from the scope of the invention as defined by the following claims.

What is claimed is:

1. An inspection system for inspecting an inside diameter (ID) surface of a component, comprising:
    a mount configured to hold the component in a first fixed position during a scanning interval;
    optics configured to direct a source light beam to said ID surface wherein an image beam is produced; and
    a line scan camera disposed in a second fixed position during said scanning interval configured to acquire said image beam.

2. The inspection system of claim 1 further including a light line generator configured to generate said source light beam, said source light beam comprising a light line.

3. The inspection system of claim 2 wherein said light line generator is centered about a main viewing axis.

4. The inspection system of claim 2 wherein a rotating axis of one of said first mirror and said scanning mirror is parallel to said source light beam.

5. The inspection system of claim 1 wherein said optics further include a beam splitter configured to facilitate the overlapping of the path taken by the source light beam and the path taken by the image beam.

6. The inspection system of claim 5 further including a lens.

7. The inspection system of claim 6 wherein said lens has a principal axis that is coincident with said main viewing axis.

8. The inspection system of claim 1 further including means for recording said image beam.

9. An inspection system for inspecting an inside diameter (ID) surface of a component, comprising:
    a mount configured to hold the component in a first fixed position during a scanning interval;
    optics configured to direct a source light beam to said ID surface wherein an image beam is produced; and
    a line scan camera disposed in a second fixed position during said scanning interval configured to acquire said image beam wherein said optics comprise,
    a first mirror moveable between a first position and a second position;
    a scanning mirror moveable from a start orientation to a stop orientation;
    said first mirror in said first position configured to direct said source light beam to said scanning mirror via a first stationary mirror, said scanning mirror configured to scan said ID surface using said source light beam when moving from said start orientation to said stop orientation.

10. The system of claim 9 wherein said start and stop orientations are first start and stop orientations, said scanning mirror further having second start and stop orientations, said first mirror in said second position being configured to direct said source light beam to said scanning mirror via a second stationary mirror, said scanning mirror being configured to scan said ID surface when moving from said second start orientation to said second stop orientation, an area of said ID surface scanned by said scanning mirror via said second stationary mirror different from that scanned by said scanning mirror via said first stationary mirror.

11. The inspection system of claim 9 wherein said line scan camera has a line of sight coincident with a main viewing axis.

12. The inspection system of claim 10 wherein said first and second stationary mirrors are symmetric about said main viewing axis.

13. The inspection system of claim 9 wherein respective rotating axes of said first mirror and said scanning mirror are parallel.

14. The inspection system of claim 10 wherein said first and second stationary mirrors are configured to direct said image beam of said component to said first mirror and said beam splitter.

15. The inspection system of claim 10 further including a control device configured to control and coordinate movements of said first mirror and said scanning mirror.

16. The inspection system of claim 15 further including means for analyzing said image beam for predetermined characteristics.

17. A method for inspecting an exemplary component for imperfections comprising the steps of:
    affixing an exemplary component to a stationary mounting platform;
    generating at least one light line;
    directing said at least one light line onto a first highly reflective surface that pivots between a first position and a second position;

further directing said at least one light line onto a first one of a pair of stationary highly reflective surfaces;

further directing said at least one light line onto a second highly reflective surface which is moveable so as to sweep from a first start orientation to a first stop orientation thereby producing an image beam corresponding a surface of at least one portion of an inside diameter (ID) of the exemplary component;

directing said image beam onto said second highly reflective surface;

further directing said image beam onto the first one of the pair of stationary highly reflective surfaces;

further directing said image beam onto said first highly reflective surface; and viewing said image beam with a stationary line scan camera.

18. The method of claim 17 further comprising the step of scanning said at least one light line across at least one portion of an exemplary component corresponding to the first start and stop orientations of said second highly reflective surface.

19. The method of claim 17 further comprising the step of symmetrically aligning said first position and said second position of said first highly reflective surface.

20. The method of claim 18 further comprising the step of rotating said second highly reflective surface from a second start orientation to a second stop orientation such that said second highly reflective surface scans at least one additional portion of said exemplary component.

21. The method of claim 17 further comprising the step of directing said light line onto at least one beam splitter.

22. The method of claim 17 further comprising the step of directing said image beam onto at least one beam splitter.

23. An inspection system for imaging a component comprising:

image acquisition means for acquiring an image beam corresponding to an exemplary component;

light source means for producing an illumination beam; and optics means for directing said illumination beam to an inside diameter (ID) surface of said exemplary component wherein said image beam is reflected therefrom, said optics means further configured to direct said image beam to said image acquisition means, wherein said image acquisition means and said exemplary component are stationary during a scanning interval.

24. The system of claim 23 wherein said image acquisition means include a lens, a stationary line scan camera and a display monitor wherein said lens magnifies and focuses said image beam as needed, said stationary line scan camera processes said image beam and said display monitor provides means for viewing said image beam.

25. The system of claim 24 further including a means for recording said image beam.

26. An inspection system for imaging a component comprising:

image acquisition means for acquiring an image beam corresponding to an exemplary component;

light source means for producing an illumination beam; and optics means for directing said illumination beam to an inside diameter (ID) surface of said exemplary component wherein said image beam is reflected therefrom, said optics means further configured to direct said image beam to said image acquisition means, wherein said image acquisition means and said exemplary component are stationary during a scanning interval, wherein said optics include a beam splitter, a pivoting mirror, a scanning mirror and a pair of stationary mirrors, said pivoting mirror having a first position configured to direct said illumination beam to said scanning mirror and said image beam from said scanning mirror via a first one of said pair of stationary mirrors, said pivoting mirror being movable from said first position to a second position configured to direct said illumination beam to said scanning mirror and to direct said image beam from said scanning mirror via a second one of said pair stationary mirrors.

27. The system of claim 26 further including a controller configured to direct movement of said pivoting mirror between said first and second positions.

28. The system of claim 26 further including a controller configured to direct movement of said scanning mirror.

* * * * *

UNITED STATES PATENT AND TRADEMARK OFFICE
CERTIFICATE OF CORRECTION

PATENT NO.   : 6,661,506 B2                                                  Page 1 of 4
DATED        : December 9, 2003
INVENTOR(S)  : Chang It is certified that error appears in the above-identified patent and that said Letters Patent is hereby corrected as shown below:

Column 5,
Line 58, after the word "Once," please delete "30."

Column 7,
Line 60, please cancel beginning with "2. The inspection system of" to and including "comprising a light line." and insert the following claim:

2.    An inspection system for inspecting an inside diameter (ID) surface of a component, comprising:
        a mount configured to hold the component in a first fixed position during a scanning interval;
        optics configured to direct a source light beam to said ID surface wherein an image beam is produced; and
        a line scan camera disposed in a second fixed position during said scanning interval configured to acquire said image beam wherein said optics comprise,
            a first mirror moveable between a first position and a second position;
            a scanning mirror moveable from a start orientation to a stop orientation;
            said first mirror in said first position configured to direct said source light beam to said scanning mirror via a first stationary mirror, said scanning mirror configured to scan said ID surface using said source light beam when moving from said start orientation to said stop orientation.

Line 63, please cancel beginning with "3. The inspection system of claim 2" to and including "main viewing axis." and insert the following claim:

3.    The system of claim 2 wherein said start and stop orientations are first start and stop orientations, said scanning mirror further having second start and stop orientations, said first mirror in said second position being configured to direct said source light beam to said scanning mirror via a second stationary mirror, said scanning mirror being configured to scan said ID surface when moving from said second start orientation to said second stop orientation, an area of said ID surface scanned by said scanning mirror via said second stationary mirror different from that scanned by said scanning mirror via said first stationary mirror.

after the word "wherein" please delete "a rotating axis of one of said first mirror and said scanning mirror is parallel to said source light beam" and insert-- said line scan camera has a line of sight coincident with a main viewing axis- Line 65, after the word "wherein" please delete "a rotating axis of one of said first mirror and said scanning mirror is parallel to said source light beam" and insert -- said line scan camera has a line of sight coincident with a main viewing axis --.

UNITED STATES PATENT AND TRADEMARK OFFICE
CERTIFICATE OF CORRECTION

PATENT NO. : 6,661,506 B2
DATED : December 9, 2003
INVENTOR(S) : Chang

It is certified that error appears in the above-identified patent and that said Letters Patent is hereby corrected as shown below:

Column 8,
Line 1, after the word "claim" please delete "1 wherein said optics further include a beam splitter configured to facilitate the overlapping of the path taken by the source light beam and the path taken by the image beam" and insert –3 wherein said first and second stationary mirrors are symmetric about said main viewing axis—.

Line 5, after the word "claim" please delete "5 further including a lens" and insert—2 wherein respective rotating axes of said first mirror and said scanning mirror are parallel—.

Line 7, after the word "claim" please delete "6 wherein said lens has a principal axis that is coincident with said main viewing axis" and insert—1 further including a light line generator configured to generate said source light beam, said source light beam comprising a light line—.

Line 10, after the word "claim" please delete "1 further including means for recording said image beam" and insert—7 wherein said light line generator is centered about a main viewing axis—.

Line 12, please cancel beginning with "9. An inspection system" to and including "orientation to said stop orientation." and insert the following claim:
    9. The inspection system of claim 7 wherein a rotating axis of one of said first mirror and said scanning mirror is parallel to said source light beam.

Line 30, please cancel beginning with "10. The system of claim 9" to and including "via said first stationary mirror." and insert the following claim:
    10. The inspection system of claim 1 wherein said optics further include a beam splitter configured to facilitate the overlapping of the path taken by the source light beam and the path taken by the image beam.

Line 41, after the word "claim" please delete "9 wherein said line scan camera has a line of sight coincident with a main viewing axis" and insert—10 further including a lens—.

UNITED STATES PATENT AND TRADEMARK OFFICE
CERTIFICATE OF CORRECTION

PATENT NO. : 6,661,506 B2
DATED : December 9, 2003
INVENTOR(S) : Chang

It is certified that error appears in the above-identified patent and that said Letters Patent is hereby corrected as shown below:

Column 8 (cont'd),
Line 44, after the word "claim" please delete "10 wherein said first and second stationary mirrors are symmetric about said main viewing axis" and insert —11 wherein said lens has a principal axis that is coincident with said main viewing axis—.

Line 47, after the word "claim" please delete "9 wherein respective rotating axes of said first mirror and said scanning mirror are parallel" and insert —3 wherein said first and second stationary mirrors are configured to direct said image beam of said component to said first mirror and said beam splitter—.

Line 50, after the word "claim" please delete "10 wherein said first and second stationary mirrors are configured to direct said image beam of said component to said first mirror and said beam splitter" and insert —1 further including means for recording said image beam—.

Line 54, after the word "claim" please delete "10" and insert -- 3 --.

Column 10,
Line 5, please cancel beginning with "24. The system of claim 23" to and including display monitor provides means for viewing said image beam." and insert the following claim:

24. An inspection system for imaging a component comprising:
        image acquisition means for acquiring an image beam corresponding to an exemplary component;
        light source means for producing an illumination beam; and
        optics means for directing said illumination beam to an inside diameter (ID) surface of said exemplary component wherein said image beam is reflected therefrom, said optics means further configured to direct said image beam to said image acquisition means, wherein said image acquisition means and said exemplary component are stationary during a scanning interval, wherein said optics include a beam splitter, a pivoting mirror, a scanning mirror and a pair of stationary mirrors, said pivoting mirror having a first position configured to direct said illumination beam to said scanning mirror and said image beam from said scanning mirror via a first one of said pair of stationary mirrors, said pivoting mirror being movable from said first position to a second position configured to direct said illumination beam to said scanning mirror and to direct said image beam from said scanning mirror via a second one of said pair of stationary mirrors.

UNITED STATES PATENT AND TRADEMARK OFFICE
CERTIFICATE OF CORRECTION

PATENT NO.      : 6,661,506 B2
DATED           : December 9, 2003
INVENTOR(S)     : Chang It is certified that error appears in the above-identified patent and that said Letters Patent is hereby corrected as shown below:

<u>Column 10 (cont'd),</u>

Line 11,  after the word "a" please delete "means for recording said image beam" and insert— controller configured to direct movement of said pivoting mirror between said first and second positions—.

Line 13,  please cancel beginning with "26. An inspection system for imaging" to and including "second one of said pair stationary mirrors." and insert the following claim:

26.    The system of claim 24 further including a controller configured to direct movement of said scanning mirror.

Line 37,  after the word "claim" please delete "26 further including a controller configured to direct movement of said pivoting mirror between said first and second positions" and insert—23 wherein said image acquisition means include a lens, a stationary line scan camera and a display monitor wherein said lens magnifies and focuses said image beam as needed, said stationary line scan camera processes said image beam and said display monitor provides means for viewing said image beam—.

Line 40,  after the word "claim" please delete "26 further including a controller configured to direct movement of said scanning mirror" and insert— 27 further including a means for recording said image beam—.

Signed and Sealed this

Twentieth Day of April, 2004

JON W. DUDAS
*Acting Director of the United States Patent and Trademark Office*